United States Patent [19]
Reo et al.

[11] Patent Number: 5,891,476
[45] Date of Patent: Apr. 6, 1999

[54] TASTEMASKED PHARMACEUTICAL SYSTEM

[76] Inventors: Joe P. Reo, 342 Courtland Ave., Harleysville, Pa. 19438; William M. Johnson, 352 E. Butler Ave., Ambler, Pa. 19002

[21] Appl. No.: 995,466

[22] Filed: Dec. 22, 1997

[51] Int. Cl.[6] .................... A61K 9/42; A61K 9/56; A61K 9/107
[52] U.S. Cl. ............................................. 424/498
[58] Field of Search ................................ 424/498

[56] References Cited

U.S. PATENT DOCUMENTS

| | | |
|---|---|---|
| 4,102,806 | 7/1978 | Kondon et al. . |
| 4,132,753 | 1/1979 | Blichare et al. . |
| 4,384,975 | 5/1983 | Fong . |
| 4,479,911 | 10/1984 | Fong . |
| 4,483,847 | 11/1984 | Augart . |
| 4,698,232 | 10/1987 | Sheu et al. . |
| 4,755,387 | 7/1988 | Tzeghai et al. . |
| 4,797,288 | 1/1989 | Sharma et al. . |
| 4,816,265 | 3/1989 | Cherukuri . |
| 4,818,539 | 4/1989 | Shaw et al. . |
| 4,820,523 | 4/1989 | Shtohryn et al. . |
| 4,828,857 | 5/1989 | Sharma et al. .......................... 426/288 |
| 4,851,392 | 7/1989 | Shaw et al. . |
| 4,865,851 | 9/1989 | James et al. . |
| 4,894,233 | 1/1990 | Sharma et al. . |
| 4,894,234 | 1/1990 | Sharma et al. . |
| 4,894,236 | 1/1990 | Jang et al. . |
| 4,929,508 | 5/1990 | Sharma et al. . |
| 4,931,293 | 6/1990 | Cherukuri . |
| 4,933,105 | 6/1990 | Fong . |
| 4,933,183 | 6/1990 | Sharma et al. . |
| 4,935,242 | 6/1990 | Sharma et al. . |
| 4,948,622 | 8/1990 | Kokubo et al. ............................ 427/3 |
| 4,971,791 | 11/1990 | Tsau et al. . |
| 4,981,698 | 1/1991 | Cherukuri et al. ........................... 426/5 |
| 5,000,965 | 3/1991 | Killeen et al. . |
| 5,004,595 | 4/1991 | Cherukuri et al. . |
| 5,017,383 | 5/1991 | Ozawa et al. ............................ 426/498 |
| 5,023,089 | 6/1991 | Sakamoto et al. . |
| 5,023,108 | 6/1991 | Bagaria et al. . |
| 5,057,319 | 10/1991 | Gotwald et al. . |
| 5,057,328 | 10/1991 | Cherukuri et al. . |
| 5,059,416 | 10/1991 | Cherukuri et al. . |
| 5,082,667 | 1/1992 | Scoik . |
| 5,085,868 | 2/1992 | Mattsson et al. ........................ 424/490 |
| 5,154,855 | 10/1992 | Sekiguchi et al. ...................... 252/312 |
| 5,162,057 | 11/1992 | Akiyama et al. . |
| 5,286,489 | 2/1994 | Tsau et al. . |
| 5,292,522 | 3/1994 | Petereit et al. . |
| 5,320,848 | 6/1994 | Geyer et al. . |
| 5,380,535 | 1/1995 | Geyer et al. . |
| 5,399,357 | 3/1995 | Akiyama et al. . |
| 5,429,825 | 7/1995 | Reo et al. . |
| 5,443,846 | 8/1995 | Yoshioka et al. . |
| 5,494,681 | 2/1996 | Cuca et al. ............................. 424/484 |
| 5,500,227 | 3/1996 | Oshlack et al. . |
| 5,554,380 | 9/1996 | Cuca et al. ............................. 424/441 |
| 5,593,690 | 1/1997 | Akiyama et al. . |
| 5,597,844 | 1/1997 | Chauhan et al. . |
| 5,599,556 | 2/1997 | Meyer et al. ........................... 424/491 |
| 5,672,358 | 9/1997 | Tabibi et al. ........................... 424/450 |
| 5,681,577 | 10/1997 | Lech et al. . |
| 5,696,165 | 12/1997 | Armitage et al. . |
| 5,728,403 | 3/1998 | Mauger et al. . |
| 5,753,255 | 5/1998 | Chavkin et al. . |

FOREIGN PATENT DOCUMENTS

| | | |
|---|---|---|
| 0 383 406 | 2/1989 | European Pat. Off. . |
| 0 368 247 B1 | 1/1994 | European Pat. Off. . |

OTHER PUBLICATIONS

Michael J. Jozwiakowski et al., "Characterization of a Hot–Melt Fluid Bed Coating Process for Fine Granules", Pharmaceutical Research, vol. 7, No. 11, 1990, 1119–1126.

Yohko Akiyama et al., "Novel Oral Controlled–Release Microsphere Using Polyglycerol Esters of Fatty Acids", Journal of Controlled Release, 26 (1993), 1–10.

L. Juul Thomsen et al., "Prolonged Release Matrix Pellets Prepared by Melt Pelletization II. Hydrophobic Substances as Meltable Binders", Drug development and Industrial Pharmacy, 20(7), 1179–1197 (1994).

*Primary Examiner*—Shep K. Rose

[57] ABSTRACT

The present invention provides a drug delivery system containing a pharmaceutically active core and a coating of the core. The coating is comprised of a an emulsifier and a wax. The coating provides rapid dissolution and enhanced long-term stability for the pharmaceutically active ingredient.

15 Claims, 4 Drawing Sheets

TASTEMASKED PHARMACEUTICAL SYSTEM

FIELD OF THE INVENTION

The present invention relates to a drug delivery system and method for preparation. More specifically the invention relates to a pharmaceutically active core which is coated, preferably with a taste-masked coating, which also protects the pharmaceutical during storage.

BACKGROUND OF THE INVENTION

Numerous drugs are known for their unpleasant taste and the prior art has disclosed products to mask these drugs from unpleasant tastes. To be effective coatings must not merely mask the taste by overcoming the unpleasant taste but also delay the hydration of the drug until it passes the mouth and taste buds.

U.S. Pat. No. 4,797,288 discloses a drug delivery system which may be chewed or swallowed that contains a hydrophobic matrix of an emulsifier, an edible material having a melting point below 100° C. selected from a fatty acid, natural waxes, synthetic waxes and mixtures thereof. The matrix is coated with a coating consisting of fatty acids and wax combination. The coat level is 200% to 400% by weight resulting in a low drug potency. Due to the high coating levels employed and materials employed in the matrix it is expected that the drug delivery rate is retarded.

European Patent 455 391 discloses granules of polyglycerol esters and a pharmaceutically active material made in a fluidized bed. The fluidized bed is heated and the material is entrained in the heated fluidized bed until the polyglycerol esters are melted and the particles are agglomerated.

U.S. Pat. No. 5,399,357 discloses a stable controlled release pharmaceutically acceptable matrix preparation consisting of a fatty acid ester of polyglycerol and microcrystalline waxes. The drug dissolution rate is retarded resulting in prolonged release not suitable for immediate drug action in the body. The system claimed is a matrix not a coating.

Although these prior disclosures provide taste masked compounds, the described systems do not provide a dissolution rate that is suitable for a pharmaceutical product where the drug is immediately released and available for drug absorption. Those with skill in the art will appreciate that the therapeutic effect will thus be delayed, see for example, "Dissolution, Bioavailability and Bioequivalence" by H. M. Abdou, Mack Publishing Company, 1989.

Additionally, the above identified disclosures do not provide any data to show that the systems are physically stable. If the systems are not stable, the delivery of the active pharmaceutical ingredient can vary over time based on environmental conditions and the length of time the pharmaceuticals have been in storage.

Therefore alternative formulations which provide uniform, stable dissolution rates during storage in various environmental conditions but which also provide rapid dissolution once ingested is highly desirable.

SUMMARY OF THE INVENTION

In accordance with the present invention there is provided in one respect a coated particle comprising:
  a) a pharmaceutically active core;
  b) a non-polymorphic wax coating comprising:
    a naturally occurring wax which is from about 50 to about 90% by weight of the coating; and an emulsifier which is from about 10 to about 50% by weight of the coating, wherein the coated particle has a substantially stable dissolution profile for six months or more.

In a second embodiment the present invention provides a coated particle comprising:
  a) a pharmaceutically active core;
  b) a non-polymorphic wax coating comprising a naturally occurring wax which is from about 50 to about 90% by weight of the coating; and an emulsifier which is from about 10 to about 50% by weight of the coating; wherein the coated particle has a dissolution profile of greater than about 50% at 15 minutes and greater than about 90% at 60 minutes.

In another embodiment of the present invention provides a method for making fast-dissolving, coated particle comprising:
  a) providing a pharmaceutically active core;
  b) coating the active core with non-polymorphic wax coating comprising:
    a naturally occurring wax which is from about 50 to about 90% by weight of the coating; and an emulsifier which is from about 10 to about 50% by weight, wherein the coated particle has a dissolution profile which does not significantly vary for a period of about 6 months.

In a third embodiment of the invention a hydrogenated vegetable oil is incorporated into wax/emulsifier mixture.

BRIEF DESCRIPTION OF THE DRAWINGS

The foregoing invention will be better understood in examining the following drawings in connection with the Examples, wherein.

DETAILED DESCRIPTION OF THE INVENTION

Figure 1:
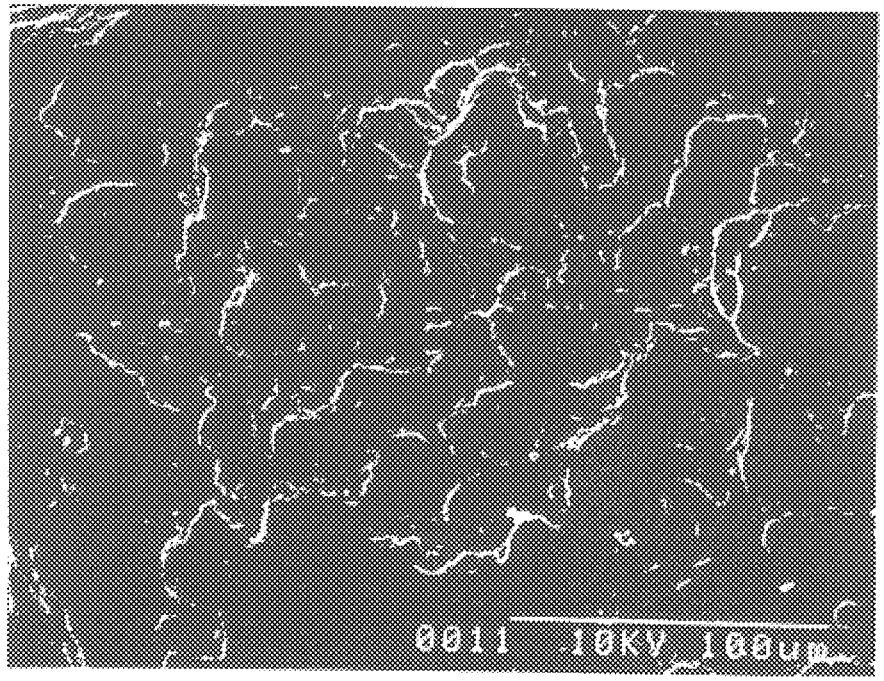
FIGS. 1–6 are plan depictions of the polymorphic structure that are common with drug delivery systems.
Figure 2:
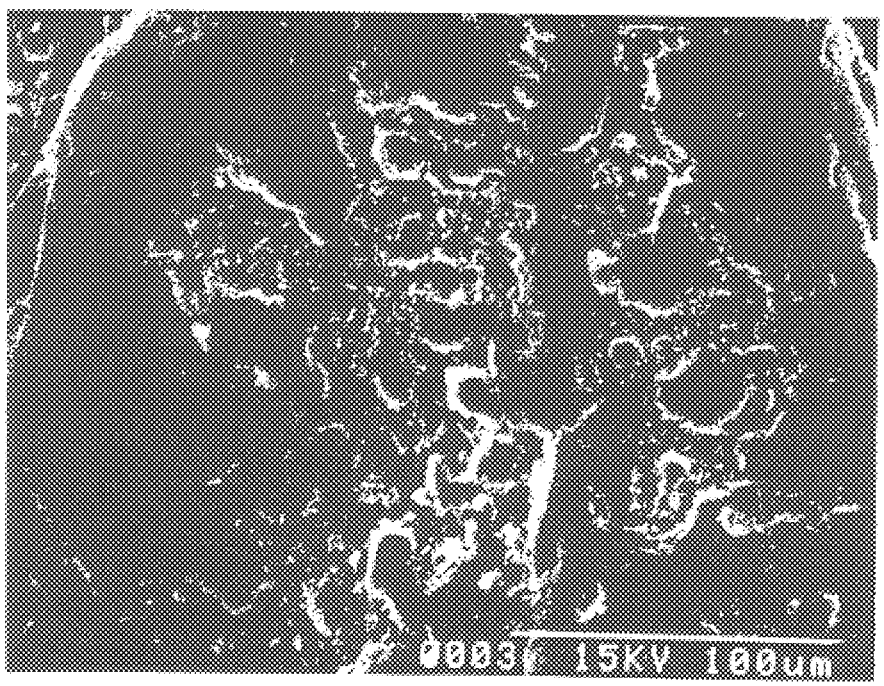
Figure 3:
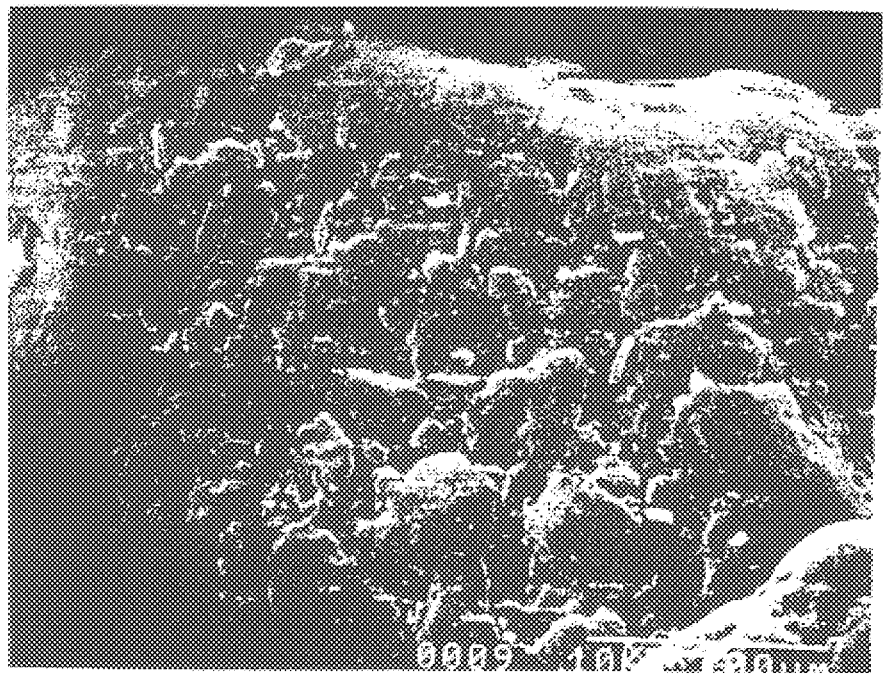
Figure 4:
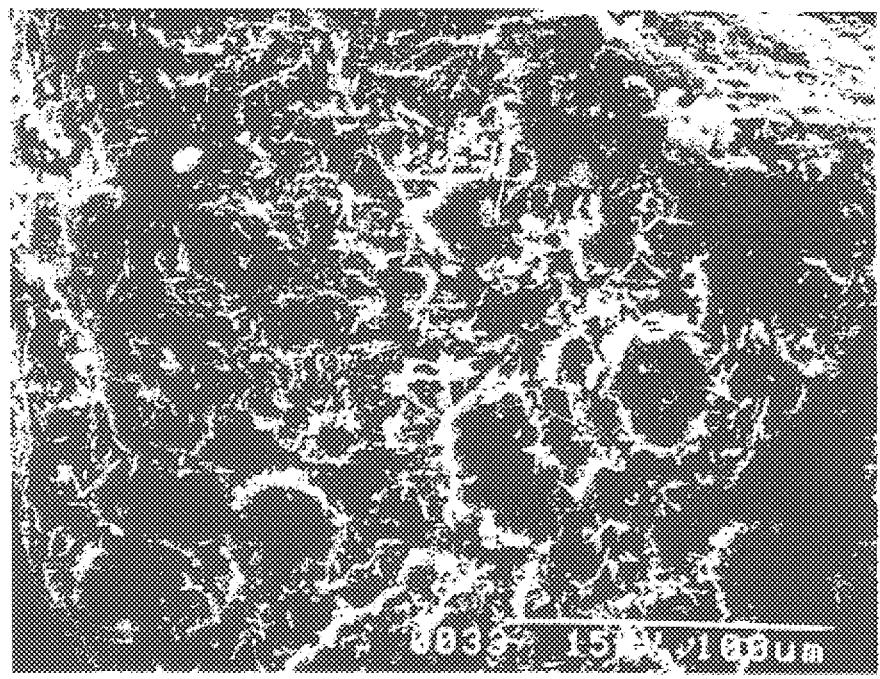
Figure 5:
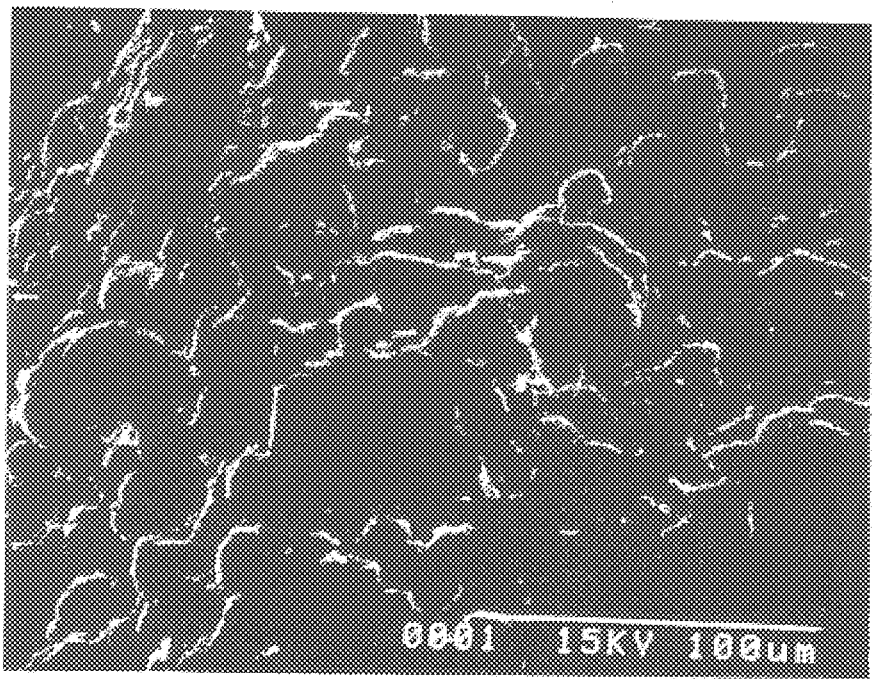
Figure 6:
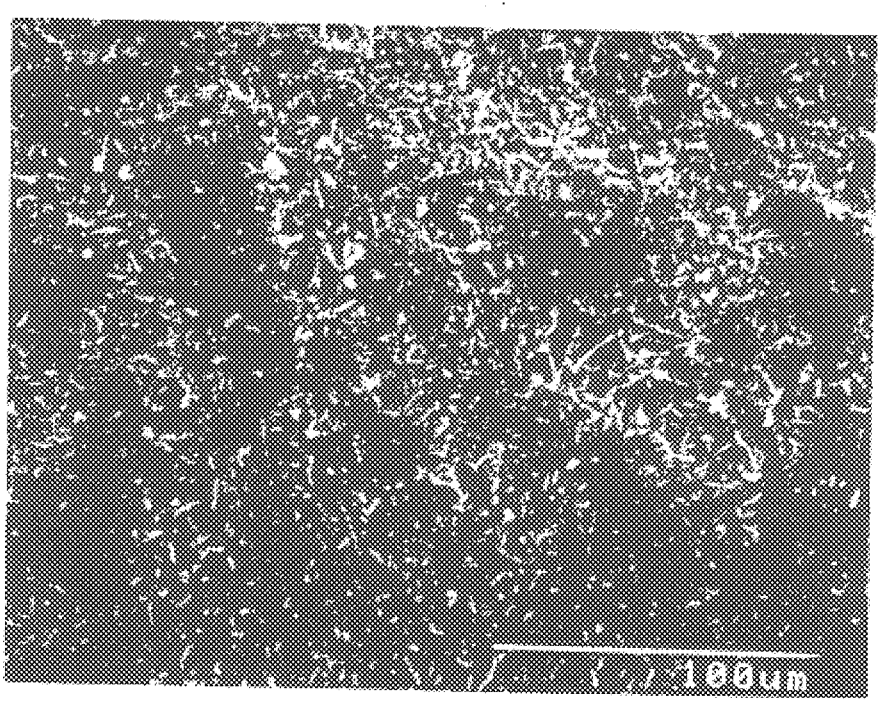

One highly desirable advantage of the present invention is the substantially stable dissolution profile the drug delivery system provides. As used throughout this application the phrase substantially stable dissolution rate shall mean that the drug delivery system of the present invention will provide a substantially constant dissolution rate for a period of six months. The dissolution rate is substantially constant, even when stored at relatively extreme conditions, such as 40° C. and 75% relative humidity. Preferably, the dissolution rate of the drug delivery system of the present invention will not vary over time by more than 5% over a six month period.

A further advantage of the present invention is that the drug delivery system has rapid dissolution rates. The dissolution rates of the drug delivery system is greater than about 50% after 15 minutes, greater than about 70% after 30 minutes and greater than about 90% after 60 minutes. As used herein, the dissolution rate of the drug delivery system is understood to be measured in USP Type II dissolution apparatus using 900 ml of a 0.01% by weight of polysorbate 80 USP TWEEN 80 (ICI America Inc.) dissolved in deionized water, agitated at 100 rpm, and as measured by ultraviolet spectrophotometry.

Without wishing to be bound to any theory the surprisingly stable dissolution rates of the present invention are believed to be related to the non-polymorphic structure of the coating ingredients of the present invention. Previously, the dissolution rates of drug delivery systems were known to vary over time and environmental conditions. Applicants have discovered that the morphology of the claimed drug delivery systems do not vary significantly over time or with changing environmental conditions. Other drug delivery systems undergo crystallinity changes, over time and with varying environmental conditions, and are defined herein as polymorphic. The drug delivery systems of the present invention are non-polymorphic. Since the drug delivery systems are non-polymorphic, the dissolution rates do not vary significantly and the dissolution rates remain stable over time and in various environmental conditions. The non-polymorphic drug delivery system is also found to be substantially pH independent. Unlike other drug delivery systems in which the delivery rate varies by pH, the present system is substantially unaffected by pH, that is the dissolution rate does not vary by more than about 5% regardless of the pH of the medium.

The particles of this invention are intended to be incorporated into a solid, non-chewed, easily swallowed dosage form since the coating barrier will fracture easily when chewed.

Useful emulsifiers in the practice of the present invention include polyglycerol esters, polysorbates, mono and diglycerides of fatty acids, propylene glycol esters, sucrose fatty acid esters and polyoxyethylene derivatives of sorbitan fatty acid esters. These emulsifiers are well known in the art and are commercially available.

Suitable polyglycerol esters include triglyceryl monostearate, hexaglyceryl distearate, hexaglyceryl monopalimate, hexaglyceryl dipalmitate, decaglyceryl distearate, decaglyceryl monoleate, decaglyceryl dioleate, decaglycerol monopalmitate, decaglycerol dipalmitate, decaglyceryl monostearate, octaglycerol monoleate, octaglycerol monostearate and decaglycerol monocaprylate.

Other useful emulsifiers include polysorbates made from the reaction product of monoglycerides or sorbitan esters with ethylene oxides. Examples of useful polysorbates include polyoxyethylene 20 mono- and diglycerides of saturated fatty acids, polyoxyethylene 4 sorbitan monostearate, polyoxyethylene 20 sorbitan tristearate, polyoxyethylene 20 sorbitan monooleate, polyoxyethylene 5 sorbitan monooleate, polyoxyethylene 20, sorbitan trioleate, sorbitan monopalmitate, sorbitan monolaurate, propylene glycol monolaurate, glycerol monostearate, diglycerol monostearate, glycerol lactylpalmitate. Most preferred emulsifiers are TWEEN 65 and TWEEN 80, both commercially available from ICI Americas Inc.

Other suitable emulsifiers include, with HLB values provided in brackets, [ ], include decaglycerol monolaurate [15.5]; decaglycerol distearate [10.5]; decaglycerol dioleate [10.5]; decaglycerol dipalmitate [11.0]; decaglycerol monostearate [13.0]; decaglycerol monooleate [13.5]; hexaglycerol monostearate [12.0]; hexaglycerol monooleate [10.5]; hexaglycerol monoshortening [12.0]; polyoxyethylene (20) sorbitan monolaurate [16.7]; polyoxyethylene (4) sorbitan monolaurate [13.3]; polyoxyethylene (20) sorbitan monopalmitate [15.6]; polyoxyethylene (20) sorbitan monostearate [14.9]; polyoxyethylene (20) sorbitan tristearate [10.5]; polyoxyethylene (20) sorbitan monooleate [15.0]; polyoxyethylene (5) sorbitan monooleate [10.0]; polyoxyethylene (20) sorbitan trioleate [11.0]. As is appreciated by those with skill in the art, the HLB value for an emulsifier is an expression of its Hydrophile-Lipophile balance, i.e., the balance of the size and strength of the hydrophilic (polar) and lipophilic (non-polar) groups of the emulsifier.

Lactic acid derivatives include sodium stearoyl lactylate and calcium stearoyl lactylate.

The hydrophilic-lipophilic balance (HLB) values of the emulsifier preferably should from about 7 to about 25, and most preferably from 10 to about 18. The emulsifier is present in amounts of about 1 to about 50% by weight and preferably about 5 to about 25% by weight of the wax/emulsifier coating.

Suitable waxes for use in the present invention include carnauba wax, synthetic carnauba wax, beeswax, lanolin wax, bayberry wax, sugar cane, candelilla wax, synthetic candelilla wax, ceresine wax, kester waxes, synthetic Japan wax, microcrystalline waxes, petrolatum waxes, carbowax wax, orange roughy wax, jojoba wax, rice bran wax, ozokerite wax, motan wax, paraffin waxes and mixtures thereof. The wax is present in amounts of about 50 to about 100% and preferably about 75 to about 95 and most preferably 80 to about 90% by weight of the coating. The most preferred wax is carnauba wax.

In an especially preferred embodiment of the present invention a hydrogenated oil, such as vegetable oil, cottonseed oil, canola oil, palm oil, palm kernel oil, and soybean oil, is incorporated into the drug delivery system. Preferably the vegetable oil is a triglyceride compound which is incorporated into the coating system at a level of from about 1 to about 80% by weight of the final coating system. It is desirable to use the hydrogenated oils because they are relatively inexpensive and widely available. Even with inclusion of the hydrogenated oils in the present invention, the coating systems remain very stable and non-polymorphic. This is surprising because the hydrogenated oils are polymorphic when used in other coating systems.

The drugs useful may be selected from a wide range of drugs and their acid addition salts. These materials can be used either singly or in combination in either a single or multiple delivery system. One or more of the active ingredients may be present within one coating or in multiple coatings contained in the product and delivered in the final coating of the present invention.

Pharmaceutically suitable salts of the active ingredient may be employed as long as the medicament retains its efficacy. Exemplary salts include hydrochloride, hydrobromide, phosphate, maleate, tartate succinate, citrate, salicylate, sulfate, acetate and the like.

The weight percentage of the drug or its acid addition salt based upon the weight of the drug and the coating is from about 50 to about 99 weight percent, preferably from about 70 to about 95 and most preferably from about 80 to about 90%. The amount of the active ingredient will vary depending upon the therapeutic dosage desired.

The present invention may be used to formulate and deliver many active medicaments that are well known in the art. U.S. Pat. No. 4,929,508 provides a suitable list of such medicaments and the relevant portions of the patent are hereby incorporated by reference. The form of the medicaments are not critical in the invention, they may be solids, liquids, powders pellets and emulsions. The only limitation as to the form of the medicament is that it must be able to be coated and contained with the drug delivery system of the present invention.

Especially preferred medicaments to be delivered by the present invention include ibuprofen, acetaminophen, aspirin, pseudoephedrine, pseudoephedrine hydrochloride, chlorpheniramine maleate, dextromethorphan hydrobromide, diphenhydramine, loratadine, phenylpropanolamine and diphenydramine hydrochloride.

Commonly known pharmaceutically acceptable additives for orally-administered drugs such as sweeteners, flavoring agents, dispersants, buffering agents and the like may be included in amounts that do not adversely affect the novel properties of the formulation described and claimed herein. Suitable sweeteners include sugar, sorbitol, saccharin, mannitol, glucose, aspartame and the like. Flavoring agents include peppermint, spearmint cinnamon, vanilla and the like.

The particle size of the drug deliver system should be such that the coated particles containing the medicaments are easily swallowed by both adults and children. Therefore screening the particles through a Number 30, (United States Standard sieve) (595 micron opening) to remove the oversized particles is beneficial.

The drug delivery system of the present invention is preferably prepared by the following steps. The pharmaceutically active ingredient is placed in a fluidized bed. Melted wax, emulsifier along with other ingredients are stirred together. The emulsifier/wax mixture is then added to the fluidized bed. The type of fluidized bed is not critical, top spray, Wurster and rotor type, fluidized beds may be employed in the present invention. The fluidized bed should provide an air stream of at least about 40°–60° C. above the melting temperature of the emulsifier/wax mixture. An atomization air temperature of about 125° C. is adequate for most systems. The melted coating material is delivered into the fluidized bed under pressure through a nozzle to create droplets of the emulsifier/wax mixture. The addition of the emulsifier/wax system is then applied to the surface of the pharmaceutically active ingredient. Another advantage of the present invention is that no solvents, either water or non-aqueous, are required in order to prepare the drug delivery system.

After the above ingredients, along with any sweeteners, tastemasking agents and other pharmaceutically acceptable ingredients, are thoroughly mixed, the coated materials typically are pressed, preferably at low pressures, into tablets.

The invention will now be illustrated by, but is not intended to be limited to, the following examples. In these examples it is understood that unless noted otherwise, all parts are weight percent. As used herein APAP is understood to mean acetaminophen, RH is understood to be relative humidity and RT is room temperature (approximately 23° C.).

EXAMPLE 1

The following is an example of a hot melt formulation using an emulsifier with a low HLB emulsifier(6.9 HLB value).

The following example describes a preferred composition and the method of preparation. The coating applied to the core particle provided a sufficient barrier for tastemasking.

| Ingredient | % (W/W) | g/batch |
| --- | --- | --- |
| Acetaminophen USP Special Granular (Mallinckrodt Code No. 1617) | 88.0 | 5000.0 |
| Carnauba Wax NF | 11.4 | 647.9 |
| Triglyceryl Monostearate | 0.6 | 34.1 |

The carnauba wax and triglyceryl monostearate were melted and mixed in a stainless steel vessel. The acetaminophen was added to the product container of a fluidized bed, Glatt GPCG 5 top spray unit. The unit was hydraulically pressed and the supply air temperature was adjusted to approximately 10°–15° below the melting point of the carnauba wax. The acetaminophen was fluidized and the exhaust air flow control flap adjusted to attain an air flow that maintained proper fluidization. The carnauba wax/triglyceryl monostearate mixture were pumped through heated transfer lines to the nozzle where it was atomized with heated air and applied to the core particles. The below table characterizes the particle size of the coated granules.

| U.S. Standard Sieve No. | Weight Percent Retained |
| --- | --- |
| 20 | 0.8 |
| 30 | 2.7 |
| 40 | 3.1 |
| 50 | 47.5 |
| 60 | 34.0 |
| 80 | 12.0 |
| pan | 0.0 |

The dissolution analysis was performed after the granules were passed through a No. 30 U.S. standard sieve using the following conditions: USP Apparatus II; Dissolution Medium 900 ml. 0.01% TWEEN 80; Paddle Speed 100 RPM. Analysis on the resulting product was performed by ultraviolet spectrophotometry. The table below indicates the level of active ingredient released over time.

| Time (min.) | % Released |
| --- | --- |
| 15 | 47 |
| 30 | 76 |
| 60 | 91 |

EXAMPLE 2

Four hot melt formulations are provided below as well as their dissolution rates. The stored samples were placed in sealed polyethylene bags and placed into environmental chamber at different temperature and humidity conditions. The storage conditions were used to accelerate the aging process.

After the appropriate time periods in the environmental chambers, the dissolution rates were measured after the granules were passed through a No. 30 U.S. standard sieve. The dissolution rate analysis was performed using the method described in Example 1.

| Trial A | | |
| --- | --- | --- |
| Ingredient | % weight/weight | grams/batch |
| Acetominophen USP Special Granular (Malinckrodt Code No. 1617) | 88.0 | 5000.0 |
| Partially hydrogenated palm oil | 9.6 | 545.6 |
| Sorbitan monostearate | 2.4 | 136.4 |

| Dissolution Results | | | | |
| --- | --- | --- | --- | --- |
| Time (minutes) | Initial % | RT 1 week | 40° C. 1 week | 40° C./75% RH 1 week |
| 15 | 26 | 25 | 18 | 17 |
| 30 | 48 | 46 | 33 | 33 |
| 60 | 72 | 72 | 57 | 56 |

-continued

Trial B

| Ingredient | % weight/weight | grams/batch |
|---|---|---|
| Acetominophen USP Special Granular (Malinckrodt Code No. 1617) | 88.0 | 5000.0 |
| Partially hydrogenated cottonseed oil | 9.6 | 545.6 |
| sodium stearoyl lactate | 2.4 | 136.4 |

Dissolution Results

| Time (minutes) | Initial % | RT 1 week | 40° C. 1 week | 40° C./75% RH 1 week |
|---|---|---|---|---|
| 15 | 57 | 55 | 72 | 34 |
| 30 | 86 | 85 | 98 | 70 |
| 60 | 98 | 97 | 101 | 94 |

Trial C

| Ingredient | % weight/weight | grams/batch |
|---|---|---|
| Acetominophen USP Special Granular (Malinckrodt Code No. 1617) | 88.0 | 5000.0 |
| STEAROTEX K (a mixture of hydrogenated caster oil and hydrogenated soybean oil) | 9.6 | 545.6 |
| Triglyceryl monostearate | 2.4 | 136.4 |

Dissolution Results

| Time (minutes) | Initial % | RT 1 week | 40° C. 1 week | 40° C/75% RH 1 week |
|---|---|---|---|---|
| 15 | 51 | 41 | 20 | 28 |
| 30 | 80 | 74 | 42 | 54 |
| 60 | 96 | 94 | 72 | 54 |

Trial D

| Ingredient | % weight/weight | grams/batch |
|---|---|---|
| Acetominophen USP Special Granular (Malinckrodt Code No. 1617) | 88.0 | 5000.0 |
| Carnuaba Wax NF | 10.6 | 600.0 |
| Sorbitan monostearate | 1.4 | 81.8 |

Dissolution Results

| Time (minutes) | Initial % | RT 1 week | 40° C. 1 week | 40° C/75% RH 1 week |
|---|---|---|---|---|
| 15 | 95 | 94 | 93 | 94 |
| 30 | 100 | 99 | 100 | 99 |
| 60 | 100 | 99 | 100 | 99 |

Figure 7:
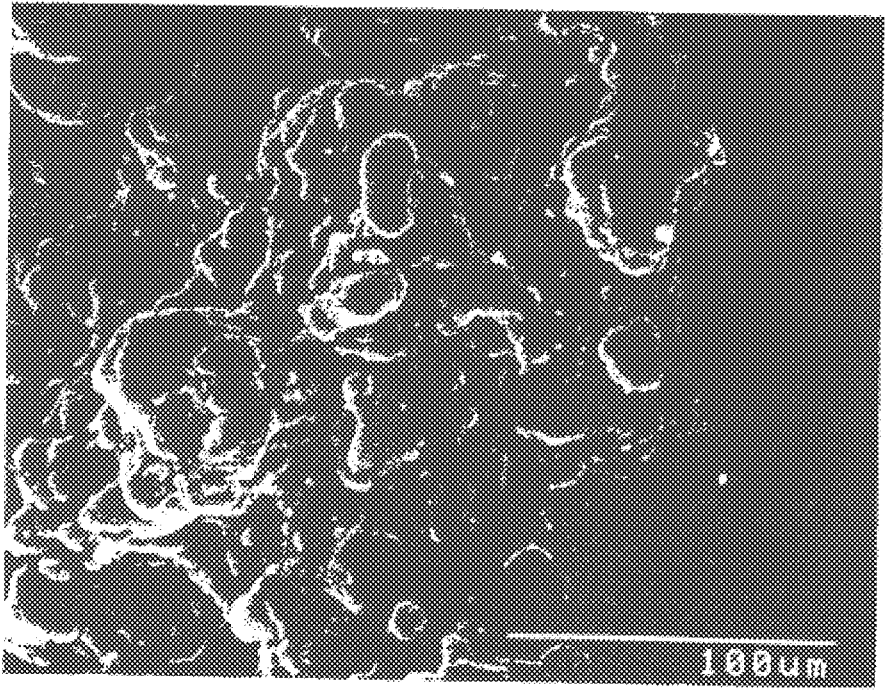
FIGS. 7 and 8 are plan depictions of the non-polymorphic structure of the present invention.
Figure 8:
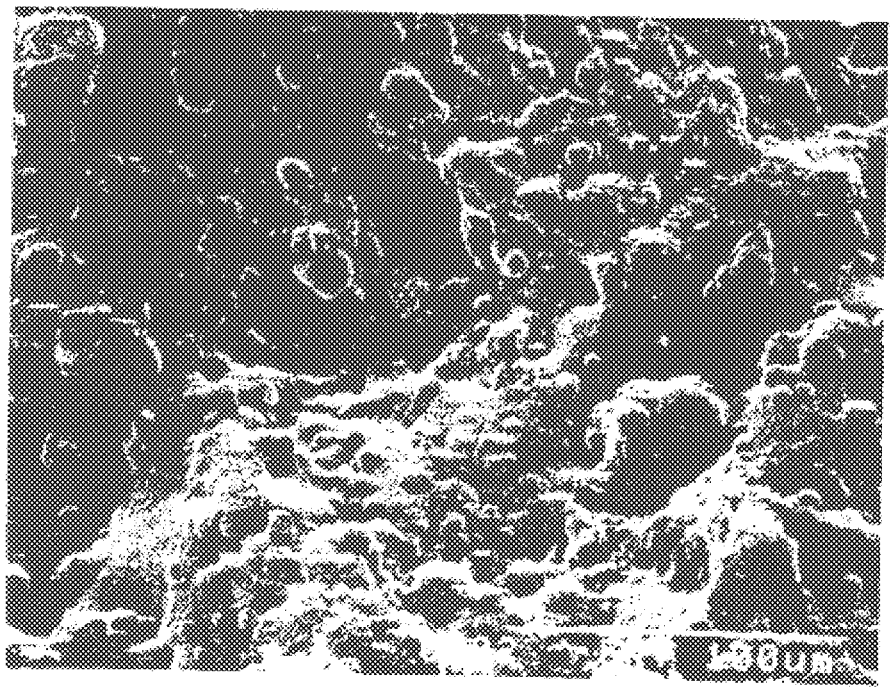

The formulations of Trials A, B, and C exhibited changes in dissolution and surface morphology as depicted in FIGS. 1–6. The drug delivery system of the present invention, example D, exhibited no polymorphic changes, FIGS. 7 and 8, and also possessed superior stability and dissolution properties.

EXAMPLE 3

An APAP coated particle was formed using STEARINE 07 (Quest International) (partially hydrogenated cottonseed oil) to form a 9.5% coating on the APAP using the method described in Example 1. The coated APAP particles were exposed to various environments and time periods. The dissolution rates were of the coated particles were measured using UV spectrophotometry.

| Time | 15 minutes | 30 minutes | 60 minutes |
|---|---|---|---|
| Room Temperature Exposure (25° C./60% relative humidity) | | | |
| Initial | 11 | 23 | 35 |
| 1 week | 9 | 18 | 35 |
| 2 weeks | 9 | 17 | 33 |
| Forty Degree Centigrade Temperature Exposure | | | |
| Initial | 11 | 23 | 35 |
| 1 week | 8 | 15 | 29 |
| 2 weeks | 7 | 14 | 27 |
| Temperature Exposure (40° C./75% relative humidity) | | | |
| Initial | 11 | 23 | 35 |
| 1 week | 8 | 14 | 28 |
| 2 weeks | 7 | 13 | 26 |

The above formulation containing the hydrogenated oil did not demonstrate fast dissolution or stability in the various environments.

An APAP coated particle was formed from a 76.5% STEAROTEX NF (Abitec Corporation) (partially hydrogenated cottonseed oil)/13.5% carnauba wax/10% TWEEN 65 coating formulation using the methodology described in Example 1. The coated APAP particles were exposed to various environments and time periods. The dissolution rates were of the coated particles were measured using UV spectrophotometry.

| Time | 15 minutes | 30 minutes | 60 minutes |
|---|---|---|---|
| Room Temperature Exposure (25° C./60% relative humidity) | | | |
| Initial | 50 | 73 | 89 |
| 7.5 months | 50 | 74 | 90 |
| 13.5 months | 52 | 77 | 93 |
| Forty Degree centigrade Temperature Exposure | | | |
| Initial | 50 | 73 | 89 |
| 1 week | 50 | 74 | 90 |
| 4 weeks | 49 | 73 | 89 |
| Temperature Exposure (40° C/75% relative humidity) | | | |
| Initial | 50 | 73 | 89 |
| 1 week | 52 | 77 | 91 |
| 7.5 months | 50 | 75 | 91 |

The drug delivery system of the present invention again provides excellent dissolution rates and dissolution stability over various environmental conditions.

EXAMPLE 4

The following example demonstrates the pH insensitivity of the present invention. The drug delivery system was a APAP USP special granular coated with carnauba wax and decaglyceryl monostearate. The weight gain of the coating was 12%. The ingredients employed were as follows:

| Ingredient | % weight/weight | grams/batch |
|---|---|---|
| APAP USP Special Granular (Mallinckrodt Code No. 1617) | 88.00 | 5000.0 |
| Carnauba Wax | 10.6 | 600.0 |
| Decaglyceryl monostearate | 1.4 | 81.8 |

The coated APAP granules were dissolved in a 7.5 pH solution (900 ml simulated intestinal fluid USP 0.01% TWEEN 80) contained in a USP Apparatus II. The paddle speed was 100 RPM and the dissolution rate analysis was performed by ultraviolet spectrophotometry. The dissolution rates were as follows:

| Time (minutes) | % released |
|---|---|
| 15 | 76 |
| 30 | 97 |
| 60 | 100 |

The coated APAP granules were dissolved in a 1.2 pH solution (900 ml simulated gastric fluid USP 0.01% TWEEN 80) using the same equipment and analysis techniques described above. The dissolution rates were as follows:

| Time (minutes) | % released |
|---|---|
| 15 | 79 |
| 30 | 97 |
| 60 | 100 |

This example demonstrates the consistent dissolution of the drug delivery system of the present invention in two very different pH systems. The lower pH system is representative of the pH found in the stomach while the higher pH system is representative of the pH found in the intestine. Regardless of the pH present, the drug delivery system of the present invention is capable of delivering consistent rates.

EXAMPLE 5

The following example describes a method for preparing dosage forms with coated particles having an active spherical core with an applied hot melt mixture coating. This hot helt mixture was a sufficient barrier for tastemasking the drug.

| Ingredient | % per unit dose | milligrams/batch |
|---|---|---|
| Hot Melt Coated Granular APAP | 63.20 | 568.2 |
| Mannitol | 32.39 | 291.2 |
| Aspartame | 2.56 | 23.0 |
| Citric Acid Anhydrous | 1.11 | 10.0 |
| Lemon Juice Flavor 27112 | 0.37 | 3.3 |
| Alpine Creme | 0.37 | 3.3 |

All ingredients were placed into a weigh boat and mixed for 5 minutes. The mixed material was placed into an aluminum pouch. This formulation is suitable for being used in a powder pack formulation.

EXAMPLE 6

The wax/emulsifier coated particles of the present invention were formulated using the following formulation:

| Ingredient | % per unit dose | milligrams/batch |
|---|---|---|
| Hot Melt Coated Granular APAP | 53.0 | 555.5 |
| Mannitol | 39.0 | 412.0 |
| Avicel pH 101 | 4.0 | 40.4 |
| Aspartame | 1.0 | 14.8 |
| Peppermint | 2.0 | 24.8 |

EXAMPLE 6

The wax/emulsifier coated particles of the present invention were formulated using the following formulation:

| Ingredient | % per unit dose | milligrams/batch |
|---|---|---|
| Hot Melt Coated Granular APAP | 53.0 | 555.5 |
| Mannitol | 39.0 | 412.0 |
| Avicel pH 101 | 4.0 | 40.4 |
| Aspartame | 1.0 | 14.8 |
| Peppermint | 2.0 | 24.8 |
| Alpine Creme | 1.0 | 8.0 |

All ingredients were placed into a weigh boat and mixed for 5 minutes. The material was then placed in a ⅜ inch die. A ⅜ round bevel edge tool was inserted into the die. Approximately 150 pounds of force was applied to the tooling using a Carver Press to make a fast dissolving wafer. The coated particles were well suited for quick dissolving, light compression dosage forms. This wax coating was a sufficient barrier for tastemasking the drug.

The specification and embodiments above are presented to aid in the complete and non-limiting understanding of the invention disclosed herein. Since many variations and embodiments of the invention can be made without departing from its scope and spirit, the invention resides in the claims hereafter appended.

What is claimed is:

1. A coated particle with a rapid dissolution rate consisting essentially of:

a) a pharmaceutically active core;
   b) a wax coating fracturing easily when chewed comprising:
      a naturally occurring wax selected from carnauba wax, beeswax, paraffin wax and mixtures thereof with non-polymorphic hydrogenated oil selected from the group consisting of vegetable oil, cottonseed oil, canola oil, palm oil, palm kernal oil and soybean oil vegetable oil which is from about 50 to about 90% by weight of the coating; and an emulsifier the emulsifier selected from polyglycerol esters, polysorbates, mono- and di-glycerides of fatty acid esters and polyoxyethylene derivatives of sorbitan fatty acid esters which is from about 10 to about 50% by weight of the coating;
   wherein the coated particle has a substantially uniform dissolution profile for six months or more, said particle prepared without water or non-aqueous solvents by applying molten droplets of the melted emulsifier and wax mixture on the surface of the active, and wherein the coated particle has a dissolution profile greater than about 50% at 15 minutes and greater than about 90% at 60 minutes the pharmaceutical active being not delayed but immediately released and available for drug absorption.

2. The coated particle of claim 1 wherein the dissolution profile does not vary more than about 5% over six months.

3. The coated particle of claim 1 wherein the emulsifier has a HLB value of from about 10 to about 25.

4. The coated particle of claim 1 wherein the wax coating additionally contains a sweetening agent.

5. The coated particle of claim 1 wherein the pharmaceutically active ingredient is selected from the group consisting of acetaminophen, ibuprofen, pseudoephedrine, pseudoephedrine hydrochloride, chlorpheniramine maleate, dextromethorphan hydrobromide, diphenhydramine and diphenhydramine hydrochloride.

6. A coated particle with a rapid dissolution rate consisting essentially of:

a) a pharmaceutically active core;

b) a wax coating fracturing easily when chewed comprising: a naturally occurring wax selected from carnauba wax, beeswax, paraffin wax and mixtures thereof with non-polymorphic hydrogenated oil selected from the group consisting of vegetable oil, cottonseed oil, canola oil, palm oil, palm kernal oil and soybean oil which is from about 50 to about 90% by weight of the coating; and an emulsifier, wherein the emulsifier is selected from polyglycerol esters, polysorbates, mono- and diglycerides of fatty acid esters and polyoxyethylene derivatives of sorbitan fatty acid esters which is from about 10 to about 50% by weight of the coating; wherein the coated particle has a substantially uniform dissolution profile of greater than about 50% at 15 minutes and greater than about 90% at 60 minutes said particle prepared without water or non-aqueous solvents by applying molten droplets of the melted emulsifier and wax mixture on the surface of the active, and wherein the coated particle has a dissolution profile greater than about 50% at 15 minutes and greater than about 90% at 60 minutes the pharmaceutical active being not delayed but immediately released and available for drug absorption.

7. The coated particle of claim 6 wherein the dissolution profile does not vary more than about 5% over six months when maintained at room temperature.

8. The coated particle of claim 6 wherein the emulsifier has a HLB value of from about 7 to about 25.

9. The coated particle of claim 6 wherein the wax coating additionally contains a sweetening agent.

10. The coated particle of claim 6 wherein the pharmaceutically active ingredient is selected from the group consisting of acetaminophen, ibuprofen, pseudoephedrine, pseudoephedrine hydrochloride, chlorpheniramine maleate, dextromethorphan hydrobromide, diphenhydramine and diphenydramine hydrochloride.

11. The coated particle of claim 1 which additionally contains a hydrogenated vegetable oil at a level of from about 1 to about 6 weight percent.

12. A method for preparing a coated particle with a raid dissolution rate consisting essentially of:

a) providing a pharmaceutically active core;

b) coating the active core with a wax coating fracturing easily when chewed comprising:

a naturally occurring wax selected from the group consisting of is carnauba wax, beeswax, paraffin wax and mixtures thereof with non-polymorphic vegetable oil selected from the group consisting of vegetable oil, cottonseed oil, canola oil, palm oil, palm kernal oil and soybean oil which is from about 50 to about 90% by weight of the coating; and an emulsifier selected from the group consisting of polyglycerol esters, polysorbates, mono- and diglycerides of fatty acid esters and polyoxyethylene derivatives of sorbitan fatty acid esters which is from about 10 to about 50% by weight;

wherein the coated particle has a dissolution profile which does not significantly vary for a period of about 6 months said particle prepared without water or non-aqueous solvents by applying molten droplets of the melted emulsifier and wax mixture on the surface of the active, and wherein the coated particle has a dissolution profile greater than about 50% at 15 minutes and greater than about 90% at 60 minutes the pharmaceutical active being not delayed but immediately released and available for drug absorption.

13. The method of claim 12 wherein the dissolution rate of the coated particle is greater than about 50% at 15 minutes and greater than about 95% at 60 minutes.

14. The method of claim 12 wherein the emulsifier has a HLB value of from about 7 to about 25.

15. The method of claim 12 wherein the pharmaceutical agent is selected from the group consisting of acetaminophen, ibuprofen, pseudoephedrine, pseudoephedrine hydrochloride, chlorpheniramine maleate, dextromethorphan hydrobromide, diphenhydramine and diphenydramine hydrochloride.

* * * * *